US010858644B2

(12) United States Patent
Laugharn, Jr. et al.

(10) Patent No.: US 10,858,644 B2
(45) Date of Patent: Dec. 8, 2020

(54) METHODS AND APPARATUSES FOR PROCESSING BLOOD AND OTHER BIOLOGICAL SAMPLES

(71) Applicant: Covaris, Inc., Woburn, MA (US)

(72) Inventors: James A. Laugharn, Jr., Boston, MA (US); Austin Purdy, Boston, MA (US)

(73) Assignee: Covaris, Inc., Woburn, MA (US)

( * ) Notice: Subject to any disclaimer, the term of this patent is extended or adjusted under 35 U.S.C. 154(b) by 75 days.

(21) Appl. No.: 15/730,088

(22) Filed: Oct. 11, 2017

(65) Prior Publication Data

US 2018/0037883 A1 Feb. 8, 2018

Related U.S. Application Data

(63) Continuation of application No. PCT/US2016/029110, filed on Apr. 25, 2016.

(60) Provisional application No. 62/153,883, filed on Apr. 28, 2015.

(51) Int. Cl.
*C12Q 1/68* (2018.01)
*C12N 15/10* (2006.01)
*C12Q 1/6806* (2018.01)
*G01N 1/34* (2006.01)
*C12Q 1/686* (2018.01)

(52) U.S. Cl.
CPC ........ *C12N 15/1003* (2013.01); *C12Q 1/6806* (2013.01); *C12Q 1/686* (2013.01); *G01N 1/34* (2013.01); *C12Q 2523/303* (2013.01)

(58) Field of Classification Search
None
See application file for complete search history.

(56) References Cited

U.S. PATENT DOCUMENTS 6,719,449 B1 * 4/2004 Laugharn, Jr. .......... B01F 11/02
366/127
2010/0041086 A1 * 2/2010 Pamula ............. B01L 3/502784
435/18
2011/0136251 A1 6/2011 Astle

OTHER PUBLICATIONS

Dineva et al. (Analyst 2007, 132, p. 1193-1199) (Year: 2007).*
(Continued)

*Primary Examiner* — Stephanie K Mummert
(74) *Attorney, Agent, or Firm* — Wolf, Greenfield & Sacks, P.C.

(57) ABSTRACT

Systems and methods for the high yield extraction and recovery of higher quality target molecule(s) (e.g., DNA, RNA, protein, lipids, metabolites) from blood spots. High quality DNA recovered from dried blood spots can be an input source for high throughput analytical methods, such as for polymerase chain reaction (e.g., qPCR) and/or next generation sequencing (NGS). In various embodiments, at least 20.0 nanograms of nucleic acid (e.g., DNA, RNA), or at least 8.0 milligrams of protein, may be extracted and recovered per an amount of dried blood corresponding to approximately 5 microliters of fresh blood. In some embodiments, a majority (e.g., greater than 50%, greater than 60%, up to 95-100%) of the nucleic acid that is extracted and recovered from the blood spot via focused acoustics may be of a quality suitable for amplification via PCR or NGS.

23 Claims, 7 Drawing Sheets

Method of Extraction and Input Amount to qPCR

(56) References Cited

OTHER PUBLICATIONS

International Search Report and Written Opinion for International Application No. PCT/US2016/029110, dated Jul. 21, 2016.
International Preliminary Report on Patentability for International Application No. PCT/US2016/029110, dated Nov. 9, 2017.
Tanna et al., Analytical Methods Used in Conjunction with Dried Blood Spots. Analytical Methods. Dec. 31, 2011;3(8):1709-18.

\* cited by examiner

METHODS AND APPARATUSES FOR PROCESSING BLOOD AND OTHER BIOLOGICAL SAMPLES

RELATED APPLICATIONS

This Application is a continuation of International Patent Application Serial No. PCT/US2016/029110, filed Apr. 25, 2016, which claims priority under 35 U.S.C. § 119(e) to U.S. Provisional Application Ser. No. 62/153,883, filed Apr. 28, 2015. The entire contents of these applications are incorporated herein by reference in their entirety.

BACKGROUND

1. Field of the Invention

Systems and methods for processing biological samples such as dried blood spots with focused acoustic energy are generally disclosed.

2. Related Art

Dried blood spots provide for a method of biosampling where blood samples taken from a patient are blotted on to a substrate (e.g., Guthrie card, filter paper) and dried for future processing and/or analysis (e.g., disease screening). For example, the dried blood spots can be archived for long-term storage at room temperature and, at a later time, may serve as a source of biomolecules such as nucleic acids, proteins, lipids, or metabolites for further analysis by methods such as DNA sequencing or high performance liquid chromatography.

Acoustic energy-based sample processing devices, such as Adaptive Focused Acoustic apparatuses made by Covaris of Woburn, Mass., are effective for homogenization and disruption of biological tissues, cells and other sample material.

SUMMARY

The present disclosure relates to methods and apparatuses for processing biological samples such as dried blood spots with focused acoustic energy. In some embodiments, a sample including blood dried on to a substrate may be placed in a vessel and subjected to focused acoustic energy applied in accordance with suitable parameters, resulting in the extraction and recovery of biomolecules from the blood in an efficient and effective manner.

For example, focused acoustical methods in accordance with the present disclosure may allow for the recovery of significantly higher yields of target biomolecules from blood spots in comparison to conventional extraction methods that do not employ such methods. Such yields may be obtained using relatively short focused acoustic treatment times (e.g., as low as approximately 2 minutes in duration). In some embodiments, at least 20.0 nanograms of nucleic acid (e.g., DNA, RNA) may be extracted and recovered per an amount of dried blood corresponding to approximately 5 microliters of fresh blood. Or, at least 8.0 milligrams of protein may be extracted and recovered per an amount of dried blood corresponding to approximately 5 microliters of fresh blood.

Methods of extracting biomolecules from blood spots or other biological samples that employ focused acoustics described herein may also result in significantly higher sample quality than that possible using conventional extraction methods. Such high quality of extracted biomolecules may provide for a comparatively greater amount of DNA that is amplifiable or otherwise useable, for example, via polymerase chain reaction (PCR) and/or next generation sequencing (NGS). In some embodiments, extraction of biomolecules from blood or other biological samples using focused acoustics may result in a greater percentage of nucleic acid extracted from a sample via the focused acoustic energy being capable of amplification via polymerase chain reaction than nucleic acid extracted from an identical sample using extraction protocol from a QIAamp DNA Mini Kit without the focused acoustic energy. In some embodiments, at least 60% of the nucleic acid (e.g., DNA) of the extracted biomolecules recovered using focused acoustical methods in accordance with the present disclosure is capable of amplification via polymerase chain reaction. For example, through exposure of a blood sample to a suitable amount of focused acoustic energy, up to 80%, 90% 95%, or 100% of the recovered DNA from the extracted biomolecules may be capable of such amplification. In certain embodiments, at least 20.0 nanograms (e.g., greater than 50.0 ng, greater than 80.0 ng, greater than 100.0 ng, greater than 120.0 ng) of nucleic acid of the extracted biomolecules may be capable of amplification via polymerase chain reaction per an amount of dried blood corresponding to approximately 5 microliters of fresh blood.

In addition to a greater level of overall recovery yield and quality of target biomolecules, focused acoustical methods of the present disclosure further allow for the DNA fragment size to be tuned as desired. Such tuning of fragment size may be particularly suitable for analytical and/or diagnostic methods, for example, the use of NGS for disease screening.

In an illustrative embodiment, a method of processing a dried blood spot or other biological sample is provided. The method may include placing a sample in a vessel, e.g., the sample including blood dried on to a substrate. The method may further include transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein at least 60% of nucleic acid of the extracted biomolecules is capable of amplification via polymerase chain reaction.

In another illustrative embodiment, a method of processing a dried blood spot is provided. The method may include placing a sample in a vessel, the sample including dried blood on a substrate. The method may include transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood. The method may further include recovering from the extracted biomolecules at least 20.0 nanograms of nucleic acid per an amount of dried blood corresponding to 5 microliters of fresh blood. Or, the method may include recovering from the extracted biomolecules at least 8.0 milligrams of protein per an amount of dried blood corresponding to 5 microliters of fresh blood.

In another illustrative embodiment, a method of processing a dried blood spot or other biological sample is provided. The method includes placing a sample in a vessel, e.g., the sample including blood dried on to a substrate. The method further includes transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein a greater percentage of nucleic acid extracted from the sample via the focused acoustic energy is capable of amplification via polymerase chain reaction than nucleic acid extracted from an identical sample using extraction protocol from a QIAamp DNA Mini Kit without the focused acoustic energy.

Acoustic energy may be used to treat a sample for a variety of purposes and in a variety of ways. For example, the acoustic energy directed to the sample may be sufficient to cause at least one of cell lysing, compound extraction, permeabilizing, stirring, catalyzing, degrading, fluidization, heating, particle breakdown, separation, extraction of biomolecules (e.g., DNA, RNA, protein, etc.), DNA shearing, and/or disruption of molecular bonds in the sample. The volume of sample treated may vary widely as well, e.g., from 10 microliters to 150 milliliters. The acoustic energy source may be spaced from and exterior to the vessel, and the acoustic energy may have a frequency of between about 100 kilohertz and about 100 megahertz and a focal zone having a width of less than about 2 centimeters.

Other advantages and novel features of the present disclosure will become apparent from the following detailed description of various non-limiting embodiments when considered in conjunction with the accompanying figures and claims.

BRIEF DESCRIPTION OF THE DRAWINGS

Aspects of the present disclosure are described with reference to the following drawings in which numerals reference like elements, and wherein.

DETAILED DESCRIPTION

Figure 1:
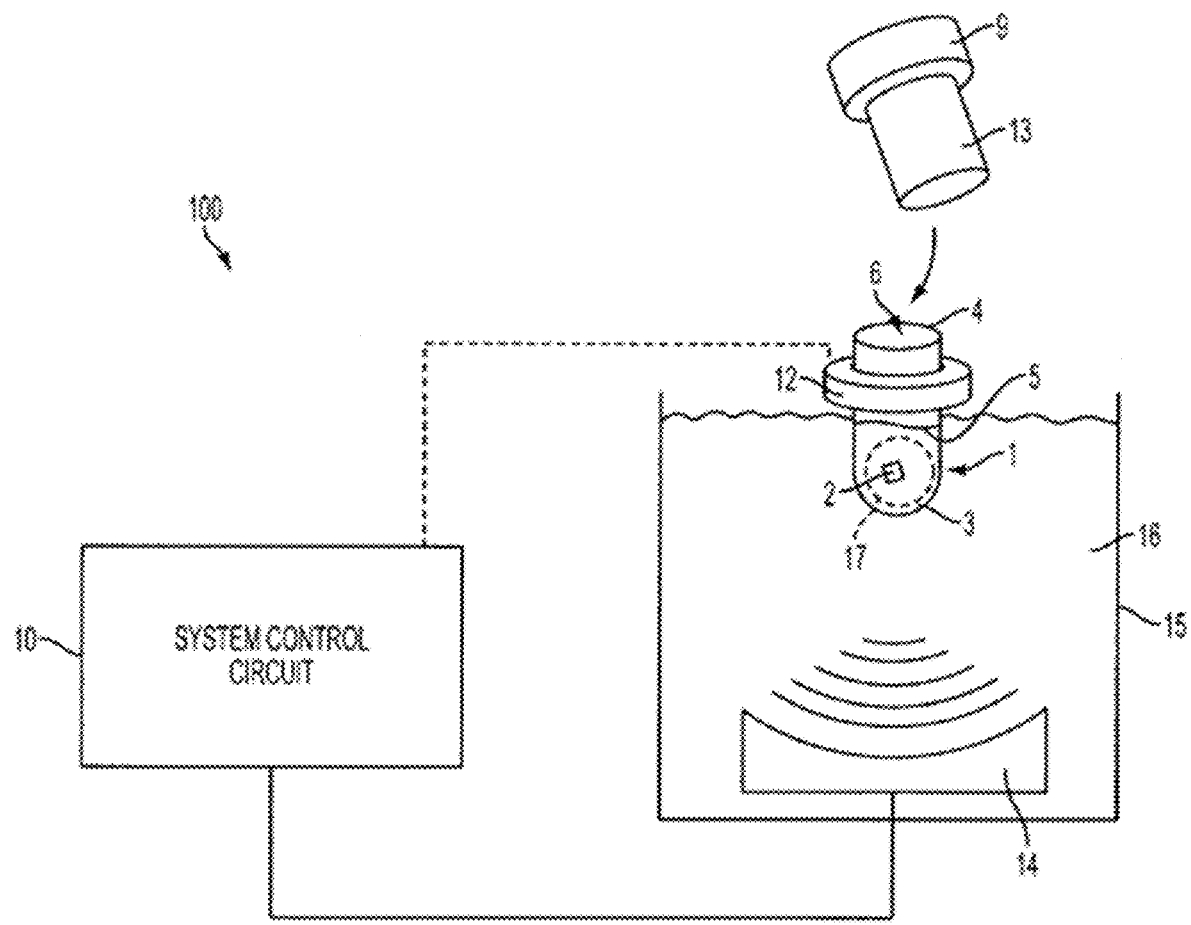
FIG. 1 shows a schematic block diagram of an acoustic treatment system that incorporates one or more aspects of the present disclosure.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, the phraseology and terminology used herein is for the purpose of description and should not be regarded as limiting.

The inventors have appreciated that it would be advantageous to employ focused acoustic energy in processing biological samples such as dried blood spots to extract and recover biomolecules efficiently and effectively. The recovered biomolecules from the sample may be of a high enough yield and quality so as to be immediately suitable for high-throughput analysis (e.g., via NGS, PCR, etc.). This is in contrast with conventional extraction methods that do not employ focused acoustics in the manner described herein. Such conventional extraction methods have been observed to result in the recovery of biomolecules having a comparatively lower yield (e.g., recovery by mass) and lower quality (e.g., a lower percentage of DNA which is PCR amplifiable), which is unsuitable for certain types of high-throughput analysis, such as NGS.

As discussed herein, aspects of the present disclosure may allow for a greater amount of nucleic acid recovery in comparison to conventional extraction methods. In some embodiments, as discussed further below, nucleic acid may be extracted and recovered at a rate of 20.0 ng or more (e.g., up to 70.0 ng, up to 80.0 ng, up to 90.0 ng, up to 100.0 ng, up to 150.0 ng, or more) per an amount of dried blood corresponding to approximately 5 microliters of fresh blood. Hence, for greater volumes of blood, even more nucleic acid may be extracted and recovered. This is in contrast to conventional methods where for dried blood corresponding to approximately 5 microliters of fresh blood, the maximum recovery of nucleic acid has been observed to be less than 20.0 ng.

In addition, systems and methods described herein may allow for a greater amount of nucleic acid recovery relative to conventional protein extraction. In various embodiments, also described in more detail below, proteins may be extracted and recovered at a rate of 8.0 mg or more (e.g., up to 10.0 mg, up to 12.0 mg, up to 15.0 mg, or more) per an amount of dried blood corresponding to approximately 5 microliters of fresh blood. And similar to that discussed above with respect to nucleic acids, for greater volumes of blood, even more protein may be extracted and recovered. In contrast, conventional methods may yield a protein recovery of less than 8.0 mg for dried blood corresponding to approximately 5 microliters of fresh blood.

As noted above, embodiments of the present disclosure allow for the extraction and recovery of a greater amount of amplifiable or useable DNA (i.e., higher quality) from a dried blood spot than previously before possible using existing methods. In some embodiments, at least 60% of the nucleic acid (e.g., DNA, RNA) that is extracted and recovered using suitable focused acoustical methods may be capable of amplification via PCR (e.g., quantitative PCR). In some cases, up to 90-100% of the recovered nucleic acid using an appropriate protocol involving extraction via focused acoustics is capable of such amplification. On the other hand, less than 50% of nucleic acid extracted and recovered using conventional methods may be capable of amplification through PCR. In various embodiments, greater than 20.0 ng or more (e.g., up to 70.0 ng, up to 80.0 ng, up to 90.0 ng, up to 100.0 ng, up to 150.0 ng, or more) of the nucleic acid may be capable of amplification via PCR per an amount of dried blood corresponding to approximately 5 microliters of fresh blood. In other words, amplifiable nucleic acid may be extracted from a dried blood sample at a rate of 20 ng or more per an amount of dried blood corresponding to 5 microliters of fresh liquid blood. And more amplifiable nucleic acid may be extracted from a blood sample having a greater volume. By contrast, less than 20.0 ng of the nucleic acid extracted and recovered from a comparable sample using conventional methods per an amount of dried blood corresponding to 5 microliters of fresh liquid blood may be capable of such amplification.

In various embodiments of the present disclosure, in extracting biomolecules from a sample of blood dried on to a substrate, the sample may be placed in a suitable vessel (e.g., microwell, process tube, Covaris microTUBE, etc.) for further processing. The substrate(s) upon which the sample is held may be provided as one or more small discs made up of an absorbent material (e.g., filter paper, porous fibrous material, etc.). The vessel well(s) may be filled with a suitable elution buffer which facilitates the release of blood from the substrate.

Generally speaking, when aiming to recover nucleic acid, an enzyme such as Proteinase K, which may be used to digest protein and remove other contamination from formulations containing nucleic acid, may be added to the mixture within the vessel. An appropriate lysis buffer may also be added at a suitable time to break down cell walls or other barriers to recovery of the target biomolecule(s). The sample may then be treated with an appropriate amount of focused acoustic energy to extract and/or further process the biomolecules, as discussed further below.

The inventors have recognized that appropriate use of focused acoustic energy enhances the overall extraction and recovery of the target molecule(s) from dried blood or other biological samples such as cells recovered from urine, sweat, feces, sputum, etc. Otherwise, without exposure to a suitable level of focused acoustics, the amount of recovery of the target molecule(s) may be substantially reduced, for example, due to inefficiencies associated with passive diffusion and lysis. The use of focused acoustics has also been observed to be more effective in overall yield and quality than other mechanical methods of agitation, such as vortex and unfocused sonication.

Various embodiments in accordance with the present disclosure will now be described in more detail. As discussed herein, such methods may be used to extract and recover from a dried blood spot increased amounts of target biomolecule(s) and having a quality such that a substantial amount of the biomolecule(s) are amplifiable (e.g., via PCR) so as to be suitable for genomic analysis, such as through NGS. However, aspects of the invention should not be interpreted narrowly in view of the blood spot examples discussed above. Instead, aspects of the invention may be used with any suitable biological sample.

A sample of fresh blood may be taken up by a suitable substrate. In some embodiments, the substrate includes filter paper, such as that provided in a conventional Guthrie card. In some embodiments, and in accordance with an aspect of the invention, the substrate includes a porous material appropriate for collecting blood. The porous material may be made up of a suitable material, for example, cellulose, biological material and/or a synthetic polymer such as polyethylene, polypropylene, polytetrafluoroethylene, polyethylene terephthalate, or combinations thereof. The porous material may be fibrous in construction and may, for example, have a porosity and/or average pore size that is suitable for wicking and/or absorbing blood thereto.

The substrate may have any other suitable characteristics. For example, the substrate may be appropriately sized so as to fit into the processing space provided by a vessel (e.g., Covaris microTUBE, vessel of a multiwell plate, etc.). The substrate may be suitably constructed so as to absorb a desired amount of blood, for example, approximately 1 microliter, approximately 5 microliters, approximately 10 microliters, or another amount. As is the case with dried blood spot analysis, the blood may be dried on to the surface (e.g., within pores) of the substrate and stored (e.g., room temperature, standard ambient conditions, less than or equal to −20 degrees C.) for later processing and analysis. Upon exposure to the focused acoustic energy, portions of the blood (e.g., cells, plasma) may be separated from the substrate and further processed (e.g., cell lysis, DNA shearing/fragmentation, etc.) via the focused acoustic treatment. Or, in some cases, certain portions of the blood may be processed while adhered to the paper.

FIG. 1 shows a schematic block diagram of an acoustic treatment system 100 that incorporates one or more aspects of the present disclosure and/or can be employed with one or more aspects of the described herein. It should be understood that although embodiments described herein may include most or all aspects of the invention(s), aspects of the invention(s) may be used alone or in any suitable combination with other aspects of the invention(s).

In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other affects in a sample 1 contained in a vessel 4. The sample 1 may include solid particles or other material 2 and/or liquid 3.

In some embodiments, the sample 1 may include blood deposited or otherwise located on the surface and/or pores of a substrate, e.g., a dried blood spot. The sample 1 may further include a solution or mixture that is suitable for lysing blood cells and extracting target biomolecules (e.g., DNA, RNA, protein, etc.). In some embodiments, the liquid 3 includes a buffer, such as water along with a detergent, e.g., a 0.25% SDS (sodium dodecyl sulfate) solution, although other solutions are possible, such as ethanol and/or other suitable buffer solutions.

Depending on the type of biomolecule(s) to be extracted, one or more enzymes or other agents may be added to the sample. In some embodiments, when extracting nucleic acid from the dried blood spot, as noted above, Proteinase K and/or other agent(s) may be added to the sample for removing contaminants, such as proteins or other molecules, from the sample. Such enzymes or agents may be added to the sample prior to, during or after focused acoustic treatment. In certain embodiments, it may be preferable for such enzymes/agents to incubate and/or be suitably mixed within the sample for a suitable period of time before activation and/or acceleration thereof. For example, Proteinase K may be added to the mixture prior to focused acoustic treatment so as to be well incorporated throughout the sample during processing. Once focused acoustic treatment has completed, the sample may be appropriately heated (e.g., 50-60 degrees C., approximately 56 degrees C.) so as to accelerate the Proteinase K enzymatic activity and remove protein or other contaminants from the target biomolecule(s).

Under the control of a control circuit 10, the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

In an embodiment where the acoustic treatment system 100 is a Covaris S220 or E220 model, acoustic treatment may be applied using a 10% duty cycle, a peak incident power of 175 watts, 200 cycles per burst, for a suitable period of time (e.g., 120 seconds or more, approximately 360 seconds). Of course, other duty cycles, peak power, cycles per burst and/or time periods may be used to produce a sufficient amount of power for processing the blood sample. For example, to achieve desirable results with regard to extraction and recovery of biomolecules from the blood sample and with regard to quality of the extracted biomolecules, the acoustic transducer may be operated at a peak intensity power of between 100 W and 300 W, a duty factor of between 10% and 90% and a cycles per burst of between 100 and 300, for an appropriate duration of time. It can be appreciated that the acoustic transducer may be operated so as to produce focused acoustic energy that results in a suitable level of energy input to the sample material.

In some embodiments, the transducer may generate acoustic energy having a peak incident power over the course of a period of time that produces a particular amount of energy, to achieve preferred results. As described herein, the peak incident power (PIP) is the power emitted from the transducer during the active period of one cycle. The peak incident power, in some cases, may control the amplitude of the acoustic oscillations. The energy applied to the sample material may be determined from the peak incident power of the applied acoustic energy and the duration of the acoustic treatment period. In some embodiments, to suitably lyse cells and extract or otherwise operate on the target biomolecule(s) from a dried blood spot sample, the acoustic transducer may be operated so as to generate focused acoustic energy according to a peak incident power of greater than or equal to 50 Watts, greater than or equal to 100 Watts, greater than or equal to 150 Watts, greater than or equal to 200 Watts, greater than or equal to 250 Watts, greater than or equal to 300 Watts, or other values outside of these ranges.

The acoustic transducer may be operated at a suitable duty factor, in combination with other parameters, to generate focused acoustic energy that leads to preferred results. As described herein, the duty factor is the percentage of time in a cycle in which the transducer is actively emitting acoustic energy. For example, a duty factor of 60% refers to the transducer being operated in an "on" state 60% of the time, and in an "off" state 40% of the time. In some embodiments, in appropriately lysing cells and extracting/processing the target biomolecule(s) from the dried blood spot sample, the acoustic transducer may be operated at a duty factor setting of greater than or equal to 10%, greater than or equal to 20%, greater than or equal to 30%, greater than or equal to 40%, greater than or equal to 50%, greater than or equal to 60%, greater than or equal to 70%, or greater than or equal to 80%, or other values outside of these ranges.

The acoustic transducer may be operated according to a suitable cycles-per-burst setting to achieve preferred results. As described herein, the cycles per burst (CPB) is the number of acoustic oscillations contained in the active period of one cycle. In some embodiments, to lyse and extract/process the target biomolecule(s) from the dried blood spot sample, the acoustic transducer may be operated to generate focused acoustic energy according to a cycles per burst setting of greater than or equal to 50, greater than or equal to 100, greater than or equal to 150, greater than or equal to 200, or other values outside of these ranges.

After a suitable degree of focused acoustic treatment, as noted above, various enzymes or other agents may be activated and/or accelerated, resulting in the removal of certain molecules or contaminants from the mixture. For instance, as noted above, when seeking to recover nucleic acids from the sample, it may be preferable to include Proteinase K within the mixture, and accelerating enzymatic activity thereof by adjusting the temperature of the sample to approximately 56 degrees C.

When seeking to recover DNA from the sample, any suitable DNA purification protocol may be used. As an example of a DNA purification step, the sample may be centrifuged and transferred to a tube (e.g., 1 mL microfuge tube) to which a suitable binder (e.g., binding binder) and solvent (e.g., ethanol) is added and mixed. The sample may then be centrifuged and subsequently transferred to a purification column where the DNA binds thereto. The assembly may further be centrifuged and washed using appropriate buffer solutions. The DNA may then be eluted using a suitable elution buffer (e.g., Tris-EDTA, water) for releasing the DNA from the purification column.

Figure 2:
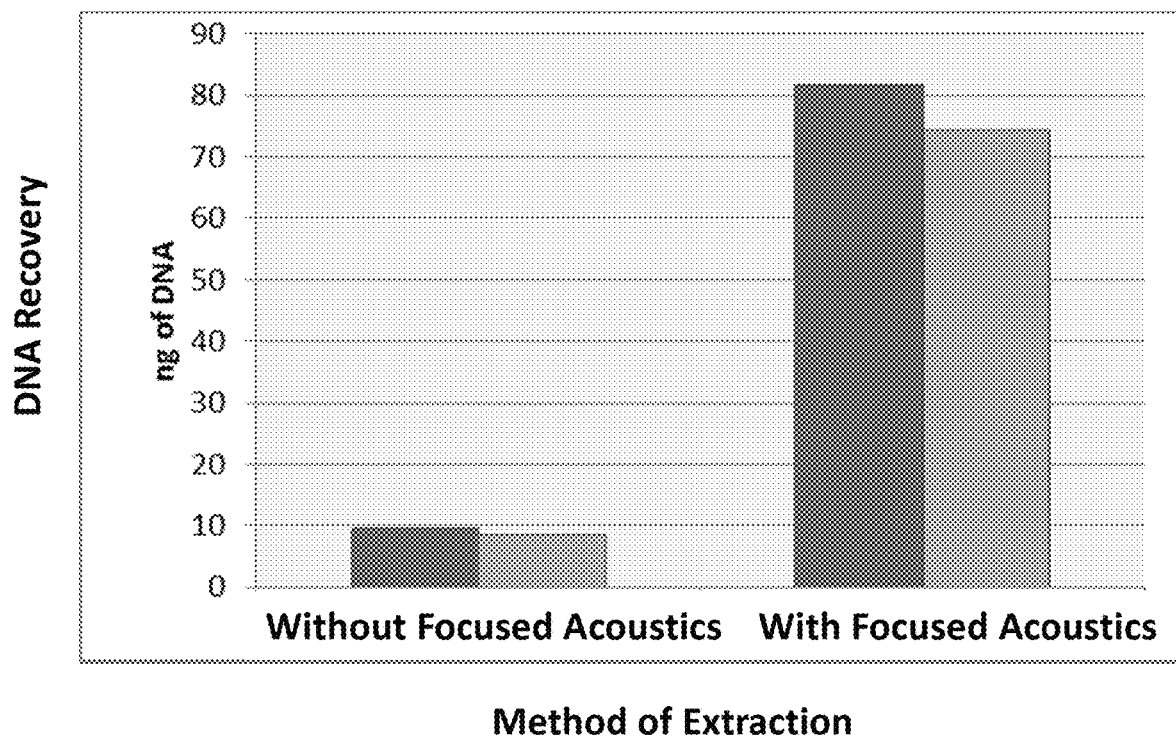
FIG. 2 depicts a comparison between amounts of DNA recovered with and without focused acoustics in accordance with some embodiments.

FIG. 2 shows a graph that depicts results from an example that compares the amount of DNA recovered for a passive extraction protocol, which does not use focused acoustics, and an active extraction protocol, which employs focused acoustics. In this example, both protocols involved extraction and recovery of DNA from a blood spot corresponding to approximately 5 microliters of fresh blood that has been dried on to a 3 mm diameter punch Guthrie card. The dried blood spot was placed in a Covaris microTUBE vessel along with an extraction mixture including appropriate amounts of SDS buffer solution, lysis buffer and Proteinase K.

In the passive extraction protocol (corresponding to bar graphs in FIG. 2 labeled "Without Focused Acoustics"), focused acoustics was not employed, and the blood spot sample was allowed to sit within the extraction mixture in the vessel for 1 hour at room temperature. In the active extraction protocol (corresponding to bar graphs in FIG. 2 labeled "With Focused Acoustics") where focused acoustics was employed, rather than sitting for 1 hour at ambient conditions, the sample was exposed to focused acoustic treatment applied using a 10% duty cycle, a peak incident power of 175 watts, 200 cycles per burst, for approximately 120 seconds. Both extraction protocols were then subject to the same DNA purification steps using a purification column, as described above. As shown, two tests were run for each protocol.

As shown in FIG. 2, the amount of DNA recovered from the dried blood spot corresponding to approximately 5 microliters of fresh blood for the passive extraction protocol (that does not employ focused acoustic energy) performed on two sample runs was about 10 ng or less. In contrast, the amount of DNA recovered from a similar dried blood spot except using the active extraction protocol (employing focused acoustic energy) for two sample runs was approximately 74 ng and 82 ng, respectively. That is, dried blood spot samples extracted via focused acoustics using the active extraction protocol resulted in a yield in DNA recovery of approximately 8 times more than that observed for dried blood spot samples that were not exposed to focused acoustics in the passive extraction protocol.

Figure 3:
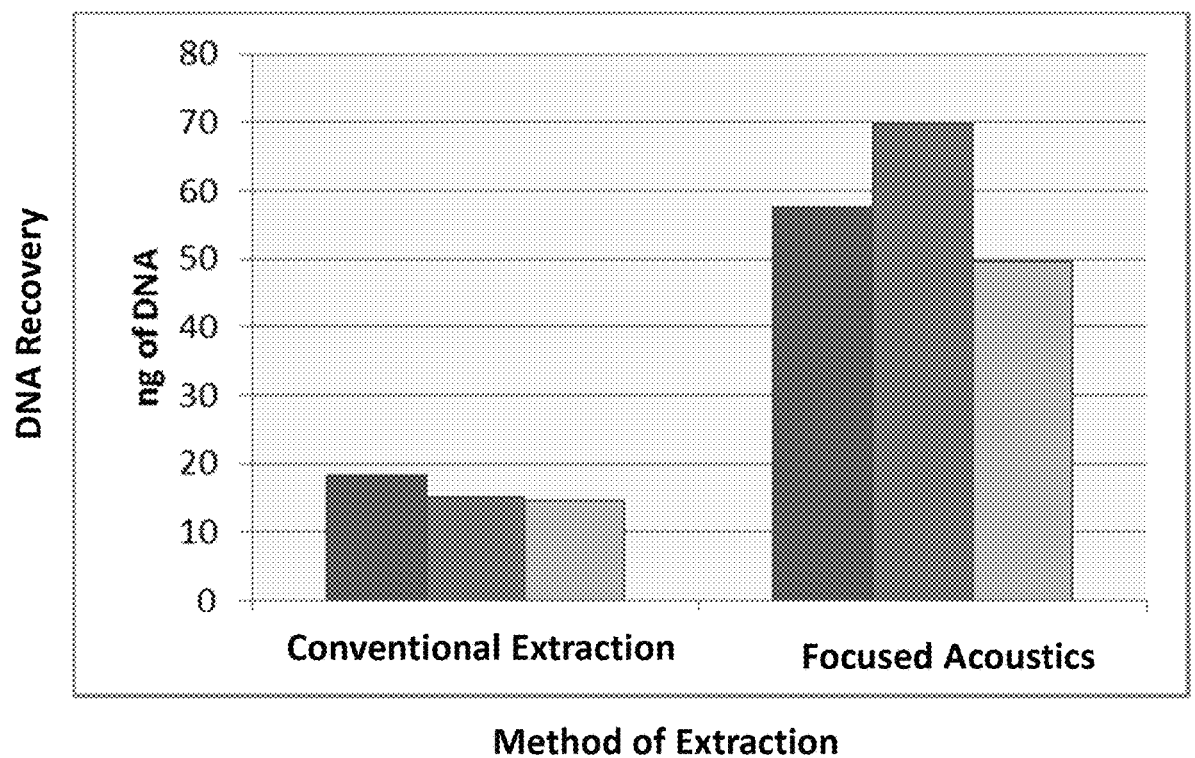
FIG. 3 shows a comparison between amounts of DNA recovered using a conventional extraction method and a focused acoustic extraction method in accordance with some embodiments.

FIG. 3 illustrates a graph that depicts results from an example that compares the amount of DNA recovered for the active extraction protocol using focused acoustic treatment as described above, as compared to a conventional method of DNA extraction (QIAamp DNA Mini Kit provided by Qiagen). As shown, three tests were run for each protocol.

As shown in FIG. 3, the amount of DNA recovered from a dried blood spot corresponding to approximately 5 microliters of fresh blood using the conventional DNA extraction kit for three trial runs was about 18 ng, 15 ng and 14 ng, respectively. In contrast, the amount of DNA recovered from a similar dried blood spot for the active extraction protocol employing the focused acoustic energy for three trial runs was approximately 50 ng, 58 ng and 70 ng, respectively. Here, the dried blood spot samples extracted via focused acoustics in the active extraction protocol resulted in a yield in DNA recovery substantially greater (e.g., approximately 3-4 times more) than that observed for dried blood spot samples that were extracted via the conventional DNA extraction method.

It can be appreciated that the active extraction protocol employing focused acoustic treatment provides enhanced ability to recover DNA from dried blood spots. Though, it can be appreciated that depending on the particular sample of blood, the amount of recoverable DNA may vary. In some embodiments, the amount of DNA recovered by using focused acoustic treatment in accordance with methods described herein per 5 microliters of fresh blood corresponding to a dried blood spot may be greater than 20.0 ng (e.g., between 20.0 ng and 160.0 ng, between 20.0 ng and 140.0 ng, between 20.0 ng and 120.0 ng, between 20.0 ng and 100.0 ng, between 20.0 ng and 80.0 ng), greater than 30.0 ng, greater than 40.0 ng, greater than 50.0 ng, greater than 60.0 ng, greater than 70.0 ng, greater than 80.0 ng, greater than 90.0 ng, greater than 100.0 ng, greater than 110.0 ng, greater than 120.0 ng, greater than 130.0 ng, greater than 140.0 ng, greater than 150.0 ng, greater than 160.0 ng, or any other suitable value outside of the above noted ranges.

Figure 4:
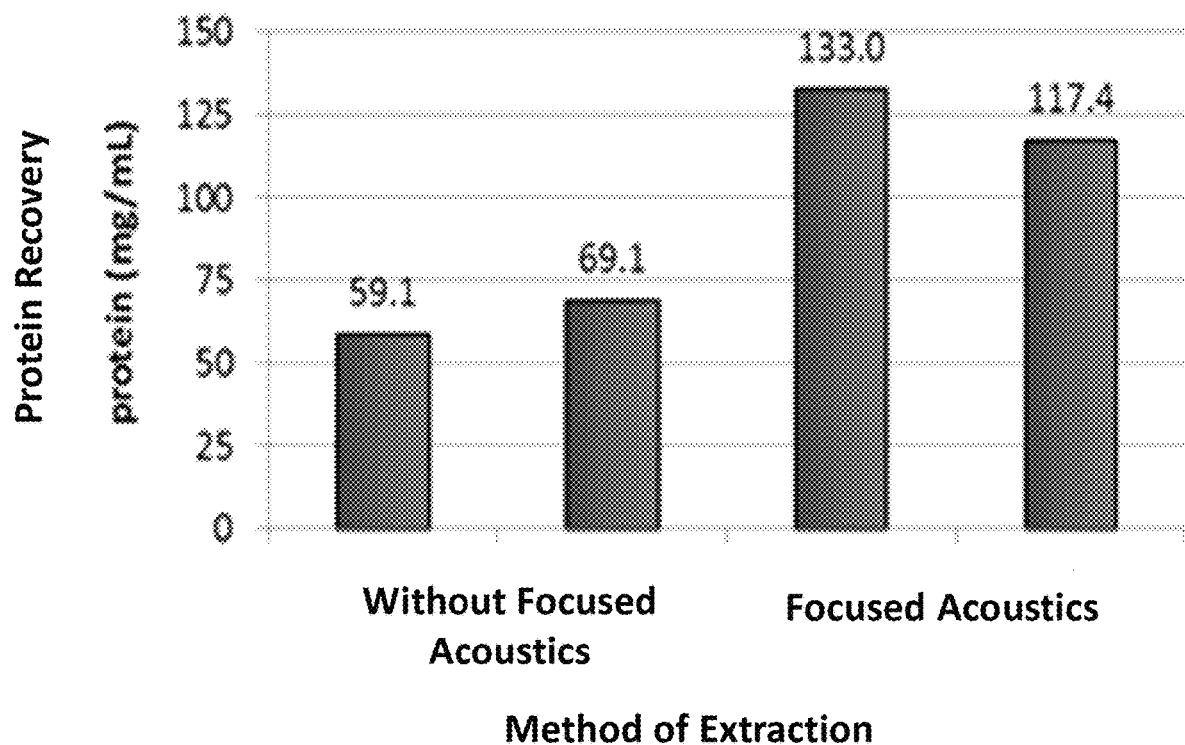
FIG. 4 shows a comparison between amounts of protein recovered with and without focused acoustics in accordance with some embodiments.

Focused acoustical methods in accordance with the present disclosure may also be effective in extraction and recovery of other types of biomolecules, such as proteins. FIG. 4 shows a graph that depicts results from an example that compares the amount of protein recovered for a passive extraction protocol, which does not use focused acoustics, and an active extraction protocol, which uses focused acoustics. In this example, both protocols involved extraction and recovery of protein from a blood spot corresponding to approximately 5 microliters of fresh blood that has been dried on to a 3 mm diameter punch Guthrie card. The dried blood spot was placed in a Covaris microTUBE vessel along with an extraction mixture including appropriate amounts of SDS buffer solution and lysis buffer, yet without Proteinase K.

Except for the absence of Proteinase K, the passive and active extraction protocols employed were similar to that described above with respect to the example of FIG. 2. Hence, in the passive extraction protocol (corresponding to bar graphs in FIG. 4 labeled "Without Focused Acoustics") where focused acoustics was not employed, the dried blood spot sample was placed within the extraction mixture for 1 hour at room temperature. In the active extraction protocol (corresponding to bar graphs in FIG. 4 labeled "With Focused Acoustics") where focused acoustics was employed, the sample was exposed to focused acoustic treatment similar to that discussed above for DNA extraction. Rather than using a purification column, which was employed for nucleic acid recovery, both protocols represented in FIG. 4 involved a Bradford assay which includes a spectroscopic analysis that measures the concentration of protein within the solution. As shown, two tests were run for each protocol.

FIG. 4 depicts the respective protein concentration of the samples recovered from a dried blood spot corresponding to approximately 5 microliters of fresh blood for both the passive and active extraction protocols. For the passive extraction protocol, the protein concentration of the final solution was measured for two trial runs to be 69.1 mg/mL and 59.1 mg/mL which, for a vessel volume of 110 microliters, corresponds to protein yields of 7.6 mg and 6.5 mg, respectively. By contrast, for the active extraction protocol, where focused acoustic treatment is applied, the protein concentration of the final solution for two trial runs was measured to be 133.0 mg/mL and 117.4 mg/mL. For a vessel volume of 110 microliters, these values correspond to respective protein yields of approximately 14.6 mg and 12.9 mg. Accordingly, dried blood spot samples extracted using focused acoustics in the active extraction protocol resulted in a yield in protein recovery of more than 2 times greater than that observed for dried blood spot samples that were not exposed to focused acoustics in the passive extraction protocol.

Similarly to that with respect to DNA extraction, use of the active extraction protocol employing focused acoustic treatment results in an enhanced ability to recover protein from dried blood spots. It can be appreciated that the amount of recoverable protein may vary depending on the particular sample of blood. In some embodiments, the amount of protein recovered by using focused acoustic treatment in accordance with methods described herein per 5 microliters of fresh blood corresponding to a dried blood spot may be greater than 8.0 mg (e.g., between 8.0 mg and 20.0 mg, between 8.0 mg and 15.0 mg), greater than 9.0 mg, greater than 10.0 mg, greater than 11.0 mg, greater than 12.0 mg (e.g., between 12.0 mg and 20.0 mg, between 12.0 mg and 15.0 mg), greater than 13.0 mg, greater than 14.0 mg, greater than 15.0 mg, or any other suitable value outside of the above noted ranges.

Figure 5:
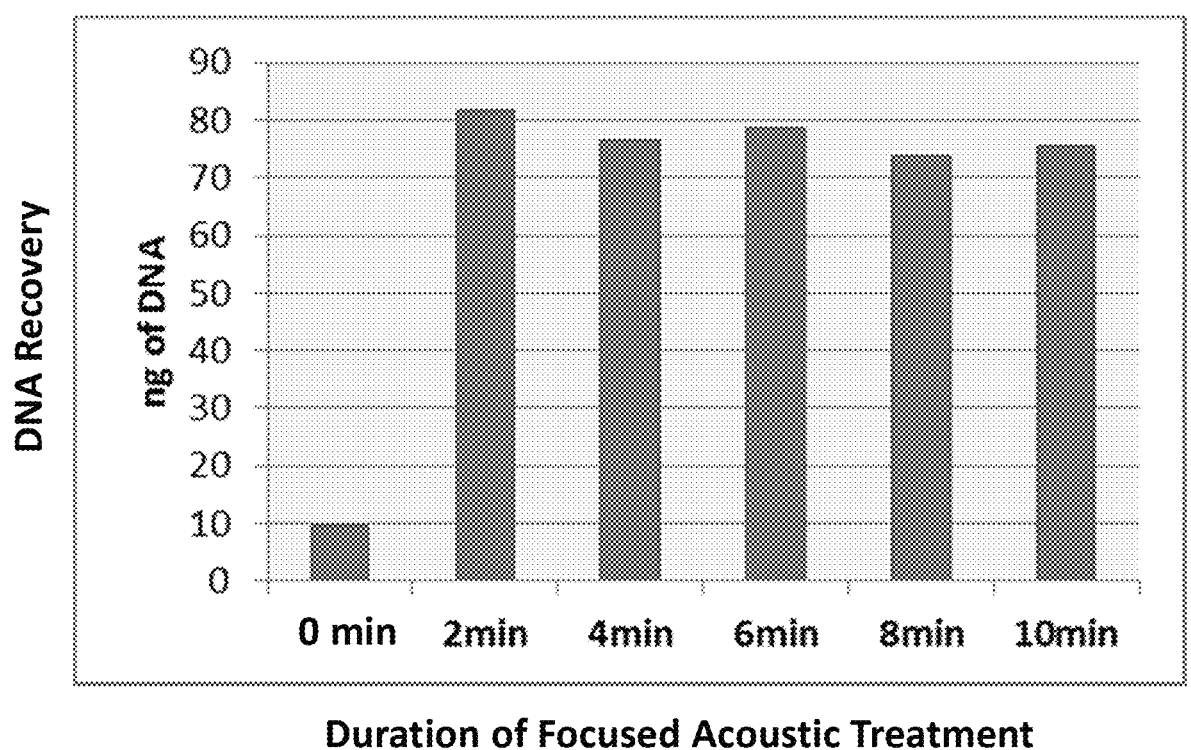
FIG. 5 depicts amounts of DNA recovered using focused acoustic extraction methods at various time intervals in accordance with some embodiments.

Exposure to a suitable level of focused acoustic energy may be helpful in bypassing a number of steps of protocol (e.g., high temperature incubation, chemical treatments, etc.) that may otherwise be required for extraction (or other processing) without the focused acoustic energy. As noted below, the focused acoustic energy may be further beneficial not only in extracting target biomolecules but also in processing the biomolecules, such as shearing and fragmentation of nucleic acids. The processing time for the target biomolecule(s) to be extracted from the sample of blood may be relatively short. For instance, as discussed above, the time under which the sample may be exposed to the focused acoustic energy for suitable recovery of the biomolecule(s) may be as low as 2 minutes. FIG. 5 depicts a graph that shows the amount of DNA recovered from a dried blood spot corresponding to 5 microliters of fresh blood using methods described above, depending on the duration of focused acoustic processing.

As shown, when the blood sample was not exposed to focused acoustic energy (i.e., duration of focused acoustic treatment is 0 minutes), only approximately 10 ng of DNA was recovered. This protocol is similar to the passive extraction protocol of FIG. 2 (labeled "Without Focused Acoustics"). Though, when the blood sample was exposed to just 2 minutes of focused acoustic energy, over 80 ng of DNA was recovered, similar to the active extraction protocol of FIG. 2 (labeled "With Focused Acoustics"). Moreover, the amount of DNA recovered upon exposure to focused acoustic energy for increasing periods of time resulted in approximately the same amount of recovered DNA. For instance, when the blood sample was exposed to 4 minutes, 6 minutes, 8 minutes and 10 minutes of focused acoustic energy, respectively, the amount of recovered DNA was within about 10% of the amount of DNA recovered when the sample was exposed to 2 minutes of focused acoustics. This shows that only a short duration of focused acoustic energy may be required for the maximum amount of DNA to be recovered from a given blood sample.

Though, it can be appreciated that for various embodiments, the duration of time in which the sample is subject to focused acoustic treatment may affect the average DNA fragment size. That is, the focused acoustic processing not only provides for extraction of the target biomolecules (i.e., nucleic acids), but also for shearing and fragmenting thereof. For example, the average DNA fragment size may decrease as the duration of acoustic energy treatment is increased and, conversely, the resulting average DNA fragment size may be larger for shorter durations of acoustic energy treatment. The average DNA fragment size may be tuned according to the duration of time under which the sample is exposed to a suitable amount of focused acoustic energy. Hence, aspects of the present disclosure allow for both extraction of DNA as well as shearing/fragmentation of the extracted DNA in a single step of focused acoustic processing. This is in contrast with conventional methods where extraction of DNA and shearing/fragmentation typically occur as separate steps.

As noted above, the type of substrate on and/or within which the blood is held may contribute to the overall ability to recover the target biomolecule(s). In some embodiments, a greater level of biomolecule recovery may be achieved for certain substrates than would otherwise be the case for other substrates. For instance, in some embodiments, a greater level of biomolecule recovery may be achieved from a substrate that is highly porous or that has a relatively large average pore size. Or, a greater level of biomolecule recovery may be achieved from a substrate or coating on the substrate made up of a hydrophilic material.

Figure 6:
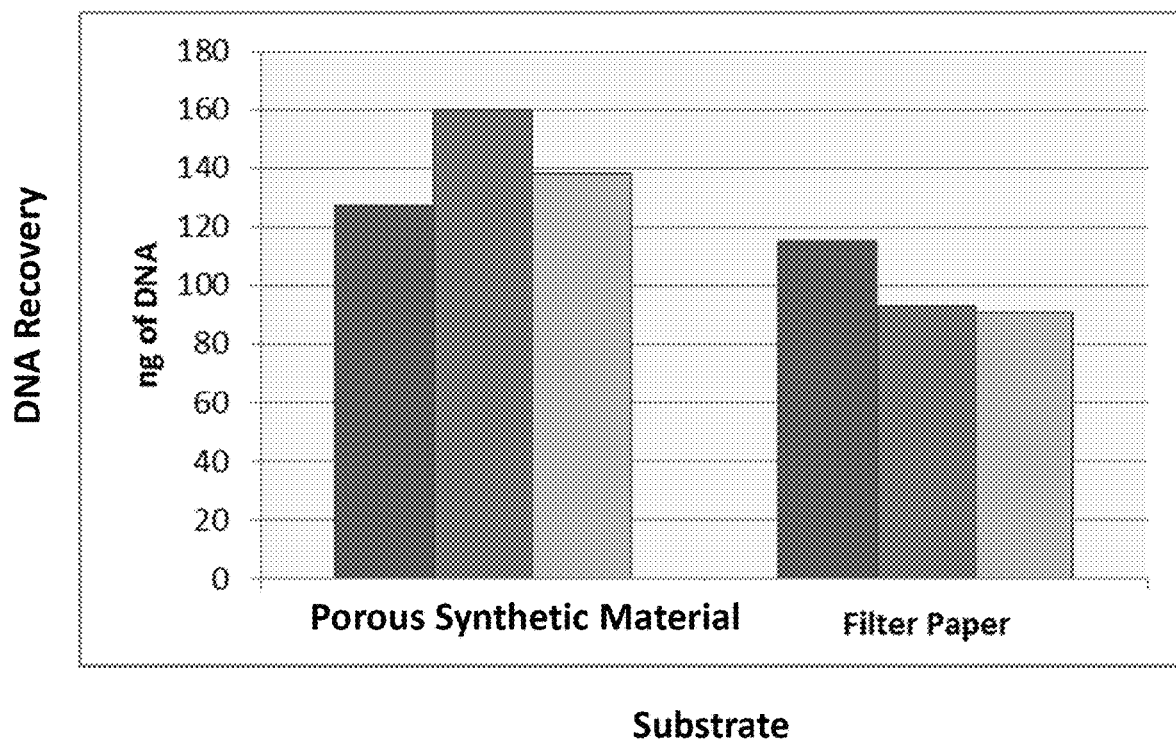
FIG. 6 shows amounts of DNA recovered using focused acoustic extraction methods using various substrates in accordance with some embodiments.

FIG. 6 shows a graph showing data from an example that compares the amount of DNA recovered from 5 microliters of fresh blood spotted on to two different substrates, a porous synthetic material and a filter paper. The samples were immersed in the extraction mixture described above and, in addition, subjected to focused acoustics at a 10% duty cycle, a peak incident power of 175 watts, 200 cycles per burst, for approximately 120 seconds. In this example, the porous synthetic material is a Porex PET fibrous rod, and the filter paper is a Guthrie card. As shown, three trial tests were run for each protocol.

Here, blood samples collected with the porous synthetic material resulted in a greater level of DNA recovery in comparison to blood samples collected with the filter paper. As shown, the amount of DNA recovered from the dried blood spot corresponding to approximately 5 microliters of fresh blood blotted on to the filter paper for three trial tests was approximately 90 ng, 95 ng and 118 ng, whereas the amount of DNA recovered from the dried blood spot corresponding to approximately 5 microliters of fresh blood blotted on to the porous synthetic material for three trial tests was substantially greater, approximately 125 ng, 140 ng and 160 ng. Thus, the type of substrate that holds the blood spotted thereon may influence the overall recovery of biomolecules from the blood sample.

In accordance with aspects of the present disclosure, due to exposure to a suitable level of focused acoustic treatment, the overall quality (e.g., ability to be amplified via PCR) of the biomolecule(s) extracted from the blood sample may be higher than the quality that would arise with a different treatment. That is, a greater percentage of nucleic acid extracted via the focused acoustic energy may be capable of amplification via polymerase chain reaction than nucleic acid extracted without the focused acoustic energy. For example, as noted above, the majority of the nucleic acid (e.g., DNA, RNA) extracted and recovered using a suitable protocol involving focused acoustics may be capable of amplification via PCR. In some embodiments, greater than 50%, greater than 60%, greater than 70%, greater than 80%, greater than 90%, greater than 95%, up to 99% or 100% of the recovered nucleic acid is capable of such amplification.

Figure 7:
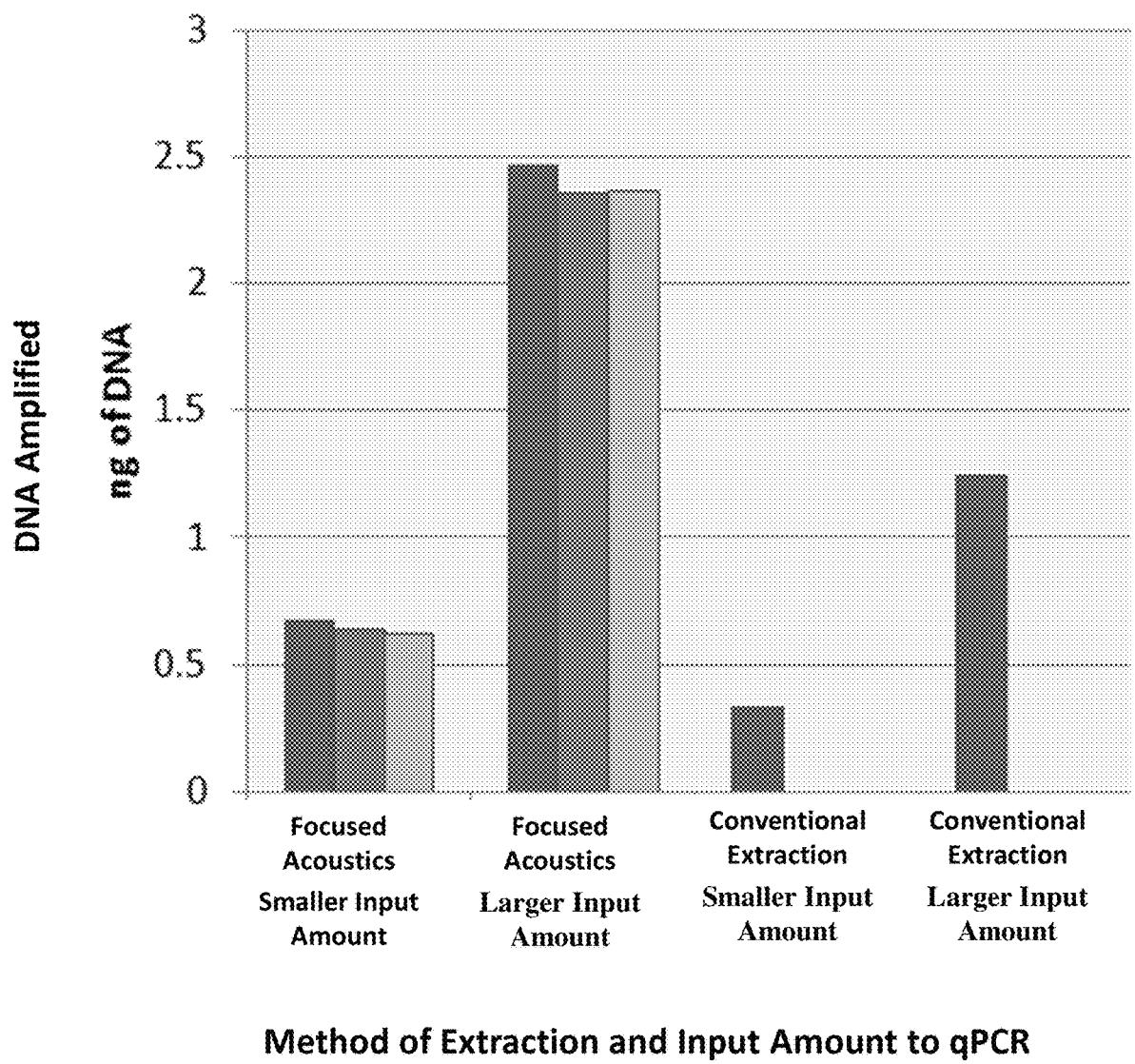
FIG. 7 depicts amounts of DNA amplified using quantitative polymerase chain reaction from various inputs of recovered DNA in accordance with some embodiments.

FIG. 7 shows a graph that shows results from an example of the amount of amplifiable or otherwise useable DNA recovered from different extraction methods as estimated from amplification of a 67-base pair amplicon via qPCR. In particular, a comparison was made of the amount of DNA that is amplifiable or otherwise useable, as recovered from an active extraction protocol that employs focused acoustics and a conventional extraction protocol (QIAamp DNA Mini Kit provided by Qiagen) that does not employ any such focused acoustic energy.

As provided herein, the QIAamp DNA Minit Kit involves the following steps. A dried blood spot sample is placed within a 1.5 mL microcentrifuge tube with 180 microliters of tissue lysis buffer (Qiagen Buffer ATL) and incubated at 85 degrees C. for 10 minutes. The tube is briefly centrifuged to remove drops from inside the lid. 20 microliters of proteinase K stock solution is added to the solution, which is mixed by vortexing, further incubated at 56 degrees C. for 1 hour, and followed by a brief centrifuge step. 200 microliters of a lysis buffer (Qiagen Buffer AL) is added to the mixture, which is mixed by vortexing, incubated at 70 degrees C. for 10 minutes, and followed by a brief centrifuge. 200 microliters of ethanol is then added to the solution, which is mixed by vortexing, and followed by a brief centrifuge step. This mixture is applied to a spin column (QIAamp Mini spin column in a 2 mL collection tube) and centrifuged at 8,000 rpm (6,000 g) for 1 minute. The spin column is removed from the filtrate and placed in a clean 2 mL collection tube. 500 microliters of wash buffer (Qiagen Buffer AW1) is added to the mixture and centrifuged at 8,000 rpm (6,000 g) for 1 minute. The spin column is removed from the filtrate and placed in another clean 2 mL collection tube. 500 microliters of wash buffer (Qiagen Buffer AW2) is subsequently added to the mixture and centrifuged at 14,000 rpm (20,000 g) for 3 minutes. The spin column is removed from the filtrate, placed in another 2 mL clean collection tube and centrifuged at full speed for 1 minute. The spin column is removed from the filtrate and then placed in a clean 1.5 mL microcentrifuge tube. 150 microliters of elution buffer (Qiagen Buffer AE) or distilled water is added to the mixture. The mixture is incubated at room temperature (15-25 degrees C.) for 1 minute and then centrifuged at 8,000 rpm (6,000 g) for 1 minute. The DNA is then collected for further processing.

In the example of FIG. 7, for DNA recovered from each of the above protocols, the amount of DNA was estimated via fluorometric quantitation with a double-stranded-DNA specific dye, and various amounts of DNA were input into a qPCR reaction (SYBR Green qPCR). In particular, a smaller amount (estimated to be approximately 0.5 ng) and a larger amount (estimated to be approximately 2.0 ng) of DNA were input, as recovered from the active extraction protocol and the conventional extraction protocol.

In addition, DNA recovered from the conventional extraction protocol was further sheared to an average fragment size of 200 bp, comparable to the average DNA fragment size provided from the active extraction protocol. In the qPCR analysis, those of skill in the art will appreciate that the number of PCR cycles needed for amplification of the DNA to reach the logarithmic phase (the Ct value) is linearly related to the logarithm of the amount of amplifiable DNA that was added to the reaction. By comparing the Ct values obtained for DNA as recovered from the active extraction protocol and the conventional extraction protocol to Ct values obtained for high-quality genomic DNA sheared to an average fragment size of 200 bp, the amount of high-quality DNA present in the DNA recovered from the active extraction protocol and the conventional extraction protocol could be estimated. By comparing the amount of input DNA estimated from qPCR analysis to the amount of input DNA estimated from fluorometric quantitation, the proportion of total DNA that is amplifiable can be estimated.

Whether or not a sample of DNA is capable of amplification depends, at least in part, on the overall quality of the DNA. For example, damage or contamination will lower the quality of a sample of DNA such that the sample is less likely to be amplified via PCR. DNA that is undamaged and/or more pure is more likely to be amplified via PCR. For example, DNA amplification can be slowed or prevented by the presence of substance(s) that can inhibit or interfere with the polymerase enzyme used in PCR, where such substances can be a by-product of the process of extracting DNA from blood dried onto a substrate.

As shown in FIG. 7, for the smaller input amount of DNA recovered via the active extraction protocol, the amount of amplifiable DNA for three trial runs was determined via qPCR to be approximately 0.6 ng. For the same input amount of DNA recovered via the conventional extraction protocol, the amount of amplifiable DNA was determined via qPCR to be approximately 0.3 ng. Thus, the amount of DNA recovered using focused acoustical methods that is capable of amplification via qPCR is approximately double that of the amount of DNA recovered using conventional extraction methods. Further, as fluorometric quantitation estimates the amount of DNA input into qPCR to be approximately 0.5 ng, the 0.6 ng output from qPCR of DNA extracted via focused acoustics implies that all or nearly all of the DNA recovered from the active extraction protocol is amplifiable or otherwise useable.

Similarly, as further shown in FIG. 7, for the larger input amount of DNA recovered via the active extraction protocol, the amount of amplifiable DNA was determined via qPCR to be as high as approximately 2.4 ng. For the same input amount of DNA recovered via the conventional extraction protocol, the amount of amplifiable DNA was determined via qPCR to be approximately 1.2 ng. Hence, approximately double the amount of DNA recovered via the active extraction protocol employing focused acoustics is capable of amplification in comparison to the amount of DNA recovered via the conventional extraction protocol that is capable of amplification. In addition, similar to that discussed above, fluorometric quantitation estimates the amount of DNA input into qPCR to be approximately 2.0 ng, and so the 2.4 ng output from qPCR of DNA extracted via focused acoustics implies that all or nearly all of the DNA recovered from the active extraction protocol is amplifiable or otherwise useable.

Accordingly, as determined via qPCR, the amount of DNA that is capable of amplification as recovered from focused acoustical methods is significantly greater than the amount of DNA that is capable of amplification as recovered from conventional extraction. Such a finding suggests that the quality and/or purity of DNA recovered from the conventional extraction protocol could be low in comparison to that of DNA which is recovered via focused acoustics and/or that substances that inhibit and/or interfere with the polymerase enzyme used in the qPCR reaction could be present in the DNA recovered by the conventional extraction protocol.

As noted above, focused acoustic methods in accordance with the present disclosure may be more effective and efficient in extracting nucleic acid (e.g., DNA) from a sample of dried blood than conventional extraction protocols, such as from a QIAamp DNA Mini Kit, which does not use such focused acoustic energy. In some embodiments, more nucleic acid extracted from a dried blood sample via methods of focused acoustic energy described herein is capable of amplification via polymerase chain reaction than nucleic acid extracted from an identical dried blood sample using extraction protocol from a QIAamp DNA Mini Kit by greater than 20%, greater than 30%, greater than 40%, greater than 50%, greater than 60%, greater than 70%, greater than 80%, greater than 90%, greater than 100%, greater than 120%, greater than 140%, greater than 160%, greater than 180%, greater than 200%; and/or less than 250%, less than 200%, less than 150%, less than 100%, less than 50%, or less than 20%. Certain combinations of the above-noted percentage ranges may be possible (e.g., between 20% and 100%, between 50% and 150%, etc.). As determined herein, extraction of biomolecules from dried blood spots via an appropriate level of focused acoustics provides for greater yield and higher quality that would otherwise be the case without such processing. This may open the door for blood spots to be a sufficient source input for higher throughput analytical methods. Such methods may include NGS where a sufficient amount of high quality DNA may be required to determine the presence of specific gene sequences, for example, in early detection disease screening for newborn babies. DNA extracted from dried blood spots (which can easily be captured at birth) is generally stable and independent of the source's age and condition. However, unlike traditional methods of DNA isolation and purification, aspects of the present disclosure allow for efficient and effective processing of blood spots to a degree where NGS and other such methods may now be possible for relatively low volume samples. The quality of DNA extracted using conventional methods is often unsuitable and can give rise to sequencing errors. Although the examples above involve the use of biological samples in the form of dried blood spots, similarly improved results are obtained using other biological samples such as cells obtained from stool, sputum, sweat, urine, tissue or other samples.

It can be appreciated that any suitable system for focused acoustic treatment may be employed. For instance, referring back to FIG. 1, the vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The transducer can be formed of a piezoelectric material, such as a piezoelectric ceramic. In some embodiments, the ceramic may be fabricated as a "dome," which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone of one of these domes may be cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as having an acoustic intensity within about 6 dB of the peak acoustic intensity, is formed around the geometric focal point. It is also possible to generate a line-shaped focal zone, e.g., that spans the width of a multi-well plate and enables the system 1 to treat multiple wells simultaneously. Other arrangements for producing focused acoustic energy are possible. For example, a flat transducer may be provided with a tapered waveguide for focusing or otherwise channeling acoustic energy emitted from the transducer toward a relatively small space where the sample and vessel are located.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

What is claimed is:

1. A method of processing a dried blood spot, comprising:
    placing a sample in a vessel, the sample including blood dried on to a substrate and a liquid; and
    transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein at least 60% of nucleic acid of the extracted biomolecules is capable of amplification via polymerase chain reaction.

2. A method of processing a dried blood spot, comprising:
placing a sample in a vessel, the sample including dried blood on a substrate and a liquid;
transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood; and
recovering from the extracted biomolecules at least 20.0 nanograms of nucleic acid per an amount of dried blood corresponding to 5 microliters of fresh blood, or recovering from the extracted biomolecules at least 8.0 milligrams of protein per an amount of dried blood corresponding to 5 microliters of fresh blood.

3. The method of claim 2, wherein at least 60% of nucleic acid of the extracted biomolecules is capable of amplification via polymerase chain reaction.

4. The method of claim 2, wherein a greater percentage of nucleic acid extracted via the focused acoustic energy is capable of amplification via polymerase chain reaction than nucleic acid extracted without the focused acoustic energy.

5. The method of claim 2, wherein at least 20.0 nanograms of nucleic acid of the extracted biomolecules per an amount of dried blood corresponding to 5 microliters of fresh blood is capable of amplification via polymerase chain reaction.

6. The method of claim 2, wherein recovering from the extracted biomolecules includes recovering between 20.0 nanograms and 160.0 nanograms of nucleic acid per an amount of dried blood corresponding to 5 microliters of fresh blood.

7. The method of claim 2, wherein recovering from the extracted biomolecules includes recovering between 8.0 milligrams and 20.0 milligrams of protein per an amount of dried blood corresponding to 5 microliters of fresh blood.

8. The method of claim 2, wherein the sample includes an amount of dried blood corresponding to less than 15 microliters of fresh blood.

9. The method of claim 2, wherein transmitting focused acoustic energy through the wall of the vessel includes exposing the blood and the substrate to focused acoustic energy for less than 10 minutes.

10. The method of claim 2, wherein the liquid includes a buffer.

11. The method of claim 2, wherein exposure of the extracted biomolecules to focused acoustic energy causes fragmenting of nucleic acid from the extracted biomolecules to an average size of less than 1000 bp.

12. The method of claim 2, wherein the transmitting focused acoustic energy includes operating an acoustic transducer at a peak intensity power of 100 W to 300 W.

13. The method of claim 2, wherein the transmitting focused acoustic energy includes operating an acoustic transducer at a duty factor of 10% to 90%.

14. The method of claim 2, wherein the transmitting focused acoustic energy includes operating an acoustic transducer at a cycles per burst of 100 to 300.

15. The method of claim 2, wherein the transmitting focused acoustic energy includes operating an acoustic transducer at a peak intensity power of between 100 W and 300 W, a duty factor of between 10% and 90% and a cycles per burst of between 100 and 300.

16. The method of claim 2, further comprising incubating the sample within the vessel at a temperature of between 20 degrees C. and 60 degrees C.

17. The method of claim 16, further comprising incubating the sample within the vessel at a temperature of between 50 degrees C. and 60 degrees C.

18. The method of claim 16, further comprising incubating the sample within the vessel at a temperature of between 20 degrees C. and 40 degrees C.

19. A method of processing a dried blood spot, comprising:
placing a sample in a vessel, the sample including blood dried on to a substrate and a liquid; and
transmitting focused acoustic energy through a wall of the vessel such that the blood and the substrate are exposed to acoustic energy having a frequency of between about 100 kilohertz and about 100 megahertz at a focal zone having a size dimension of less than about 2 centimeters, resulting in extraction of biomolecules from the blood, wherein a greater percentage of nucleic acid extracted from the sample via the focused acoustic energy is capable of amplification via polymerase chain reaction than nucleic acid extracted from an identical sample using extraction protocol from a QIAamp DNA Mini Kit without the focused acoustic energy.

20. The method of claim 1, wherein at least 20.0 nanograms of nucleic acid of the extracted biomolecules per an amount of dried blood corresponding to 5 microliters of fresh blood is capable of amplification via polymerase chain reaction.

21. The method of claim 1, wherein transmitting focused acoustic energy through the wall of the vessel includes exposing the blood and the substrate to focused acoustic energy for less than 10 minutes.

22. The method of claim 1, wherein transmitting focused acoustic energy through the wall of the vessel causes fragmenting of nucleic acid from the extracted biomolecules to an average size of less than 1000 bp.

23. The method of claim 1, wherein transmitting focused acoustic energy through the wall of the vessel includes operating an acoustic transducer at a peak intensity power of between 100 W and 300 W, a duty factor of between 10% and 90% and a cycles per burst of between 100 and 300.

* * * * *